United States Patent
Shah et al.

(10) Patent No.: US 7,501,434 B2
(45) Date of Patent: Mar. 10, 2009

(54) 6-CARBOXY-NORMORPHINAN DERIVATIVES, SYNTHESIS AND USES THEREOF

(75) Inventors: Syed M. Shah, East Hanover, NJ (US);
Kadum A. Ali, Congers, NY (US);
FangMing Kong, River Vale, NJ (US);
Tianmin Zhu, Monroe, NY (US);
Charles T. Gombar, West Chester, PA (US)

(73) Assignee: Wyeth, Madison, NJ (US)

( * ) Notice: Subject to any disclaimer, the term of this patent is extended or adjusted under 35 U.S.C. 154(b) by 25 days.

(21) Appl. No.: 11/888,955

(22) Filed: Aug. 3, 2007

(65) Prior Publication Data

US 2008/0064744 A1    Mar. 13, 2008

Related U.S. Application Data

(60) Provisional application No. 60/835,687, filed on Aug. 4, 2006.

(51) Int. Cl.
*A61K 31/485* (2006.01)
*C07D 489/02* (2006.01)

(52) U.S. Cl. .................. 514/282; 546/44; 546/46

(58) Field of Classification Search .............. 514/282; 546/44, 46

See application file for complete search history.

(56) References Cited

U.S. PATENT DOCUMENTS

| 4,176,186 A | 11/1979 | Goldberg |
|---|---|---|
| 4,719,215 A | 1/1988 | Goldberg |
| 4,861,781 A | 8/1989 | Goldberg |
| 5,102,887 A | 4/1992 | Goldberg |
| 5,811,451 A | 9/1998 | Minoia et al. |
| 5,972,954 A | 10/1999 | Foss et al. |
| 6,274,591 B1 | 8/2001 | Foss et al. |
| 6,559,158 B1 | 5/2003 | Foss et al. |
| 6,608,075 B2 | 8/2003 | Foss et al. |
| 2004/0266806 A1 | 12/2004 | Sanghvi et al. |
| 2005/0124657 A1 | 6/2005 | Christ et al. |
| 2007/0099946 A1 | 5/2007 | Doshan |
| 2007/0265293 A1 | 11/2007 | Boyd et al. |
| 2008/0064743 A1 | 3/2008 | Shah et al. |
| 2008/0070975 A1 | 3/2008 | Shah et al. |

FOREIGN PATENT DOCUMENTS

| EP | 0663401 | 7/1995 |
|---|---|---|
| WO | WO 2004/043964 | 5/2004 |
| WO | WO 2008/064150 | 5/2008 |
| WO | WO 2008/064351 | 5/2008 |
| WO | WO 2008/064353 | 5/2008 |
| WO | WO 2008/070462 | 6/2008 |
| WO | WO 2008/121860 | 9/2008 |
| WO | WO 2008/121348 | 10/2008 |

OTHER PUBLICATIONS

Yuan, Chun-Su, "Clinical status of methylnaltrexone, a new agent to prevent and manage opioid-induced side effects." Journal of Supportive Oncology, Biolink Communications, vol. 2, No. 2, Mar. 2004, pp. 111-117.
Fleischhacker, W, et al., "14-Methyl-Derivate des Morphins mit 5-, 6- oder 7gliedrigem Ring C" Monatshefte Fur Chemie, Springer Verlag. Wien, AT, vol. 108, 1977, pp. 1441-1454.
Goerlitzer, et al., "Darstellung und Charakterisierung von Bromierungsprodukten des Oxycodons" Pharmazie, Die, Govi Verlag, Eschborn, DE, vol. 47, No. 12, 1992, pp. 893-897.
Boes, et al., "A short and efficient synthesis of C-nor-dihydrocodeinone—the antipode of Goto's sinomenilone" Heterocycles, vol. 20, n0. 6, 1983, pp. 1077-1081.
Kratzel, et al., "Synthesis of 5a, 11b-propanonaphtho[1,2-e][1,2]oxazepines as potential opioid analgesics" Journal of the Chemical Society, Perkin Transactions 1, No. 11, 1994, pp. 1541-1543.
Kratzel, et al., "An efficient synthesis of 14-halogenomethyl-substituted C-normorphinans" Heterocycles, vol. 26, No. 10, 1987, pp. 2703-2710.
International Search Report, PCT/US2007/017365.

*Primary Examiner*—Charanjit S Aulakh
(74) *Attorney, Agent, or Firm*—Andrea L.C. Robidoux; Choate Hall & Stewart LLP

(57) ABSTRACT

The present invention relates to compounds of formula I, synthesis thereof, and methods of using the same.

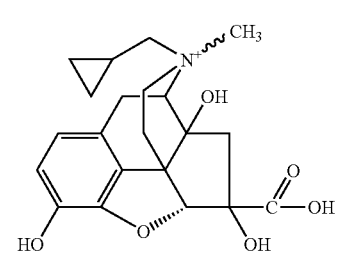

14 Claims, 4 Drawing Sheets

6-CARBOXY-NORMORPHINAN DERIVATIVES, SYNTHESIS AND USES THEREOF

CROSS-REFERENCE TO RELATED APPLICATIONS

The present application claims priority to U.S. provisional patent application Ser. No. 60/835,687, filed Aug. 4, 2006, the entirety of which is hereby incorporated herein by reference.

BACKGROUND OF THE INVENTION

Opioids have been widely used as narcotic medications that activate opioid receptors located in the central nervous system to relieve pain in patient therapy. Opioids, however, also react with receptors in the peripheral nervous system, resulting in side effects, including constipation, nausea, vomiting, urinary retention and severe itching. Most notable are the effects in the gastrointestinal tract (GI) where opioids inhibit gastric emptying and propulsive motor activity of the intestine, thereby decreasing the rate of intestinal transit, which can produce constipation. The effectiveness of opioids for pain therapy is often limited due to resultant side effects, which can be debilitating and often cause patients to cease use of opioid analgesics.

Endogenous opioid compounds and receptors may also affect activity of the gastrointestinal (GI) tract and may be involved in normal regulation of intestinal motility and mucosal transport of fluids in both animals and man. (Koch, T. R, et al., Digestive Diseases and Sciences 1991, 36, 712-728; Schuller, A. G. P., et al., Society of Neuroscience Abstracts 1998, 24, 524, Reisine, T., and Pasternak, G., Goodman & Gilman's The Pharmacological Basis of Therapeutics Ninth Edition 1996, 521-555 and Bagnol, D., et al., Regul. Pept. 1993, 47, 259-273). Thus, an abnormal physiological level of endogenous compounds and/or receptor activity may lead to bowel dysfunction.

Compounds that bind to opioid receptors (mu-, kappa- and delta-receptors) have been found useful in the treatment of diseases modulated by opioid receptors, for example, as discussed above, functional gastrointestinal disorders, including, but not limited to irritable bowel syndrome, constipation, ileus, nausea, vomiting; and pruritic dermatoses, such as allergic dermatitis and atopy in animals and humans. Compounds that bind to opioid receptors have also been indicated in the treatment of additional conditions, including eating disorders, opioid overdoses, depression, anxiety, schizophrenia, addiction and dependence disorders (e.g., smoking, alcohol, narcotic, behavioral addictions and dependencies), sexual dysfunction, shock, stroke, spinal damage and head trauma, among others.

Opioid antagonists such as naloxone, naltrexone, and nalmefene, have been studied as a means of antagonizing undesirable peripheral effects of opioids. However, these agents act not only on peripheral opioid receptors, but also on central nervous system sites, so that they sometimes reverse the beneficial analgesic effects of opioids, or cause symptoms of opioid withdrawal. Preferable approaches for use in controlling opioid-induced side effects in patients include use of peripheral opioid antagonist compounds that do not readily cross the blood-brain barrier. For example, the peripheral μ opioid antagonist compound methylnaltrexone and related compounds have been disclosed for use in curbing opioid-induced side effects in patients (e.g., constipation, pruritus, nausea, and/or vomiting). See, e.g., U.S. Pat. Nos. 5,972,954, 5,102,887, 4,861,781, and 4,719,215; and Yuan, C.-S. et al. Drug and Alcohol Dependence 1998, 52, 161. The S-methylnaltrexone compound has been isolated and found to be a peripheral μ opioid agonist, while the R-methylnaltrexone compound retains antagonist activity. See, e.g., U.S. patent application Ser. Nos. 11/441,452, filed May 25, 2006, published WO2006/127898, and 11/441,395 filed May 25, 2006, published WO2006/127899. Methylnaltrexone is commercially available. For example, methylnaltrexone is available in a powder form from Mallinckrodt Pharmaceuticals, St. Louis, Mo., provided as a white crystalline powder freely soluble in water.

Thus, identification of new therapeutic agents and methods for the treatment of side effects and/or disorders mediated by opioid receptor actions are useful for providing alternatives and/or improvements to currently available therapies.

SUMMARY OF THE INVENTION

The present invention provides newly identified N-methyl-C-normorphinan derivatives of formula I:

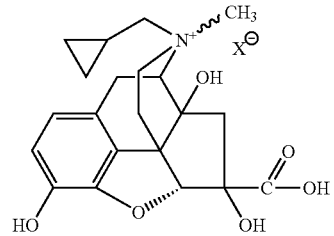

I or a pharmaceutically acceptable salt thereof. The present invention also provides pharmaceutically acceptable compositions comprising a provided compound, methods for preparation and uses thereof. Provided compounds are useful as antagonists or partial antagonists of kappa-, delta- and mu-opioid receptors.

One of ordinary skill in the art will recognize that formula I is drawn as a stereochemically generic structure intending to represent all possible stereoisomeric forms and is not intended to be limited to a racemic mixture.

In general, provided compounds of formula I, or pharmaceutically acceptable compositions thereof, are useful for preventing, treating or reducing severity of side effects resulting from use of opioids, including inhibition of gastrointestinal dysfunction (e.g., constipation, bowel hypomotility, impaction, gastric hypomotility, GI sphincter constriction, increased sphincter tone, inhibition of gastrointestinal motility, inhibition of intestinal motility, inhibition of gastric emptying, delayed gastric emptying, incomplete evacuation, nausea, emesis (vomiting), bloating, abdominal distension), cutaneous flushing, sweating, dysphoria, pruritis, urinary retention, etc. Provided compounds and compositions are useful for administration to patients receiving short term opioid treatment (e.g., patients recovering from surgery (abdominal, orthopedic, surgery from trauma injuries etc.), patients recovering from trauma injuries, and patients recovering from child birth). Provided compounds and compositions are also useful for administration to subjects receiving chronic opioid administration (e.g., terminally ill patients receiving opioid therapy (e.g., an AIDS patient, a cancer patient, a cardiovascular patient); subjects receiving chronic opioid therapy for pain management; subjects receiving opioid therapy for maintenance of opioid withdrawal).

Additional uses of provided compounds and compositions include prevention, treatment or reduction of severity of symptoms associated with disorders or conditions resulting from normal or aberrant activity of endogenous opioids. Such disorders or conditions include, among others, ileus (e.g., post-partum ileus, paralytic ileus), gastrointestinal dysfunction that develops following abdominal surgery (e.g., colectomy, including but not limited to, right hemicolectomy, left hemicolectomy, transverse hemicolectomy, colectomy takedown, and low anterior resection) or hernia repair) such as post-operative ileus, and idiopathic constipation. Provided compounds and compositions are also useful in treatment of conditions including, for example, cancers involving angiogenesis, inflammatory disorders (e.g., irritable bowel disorder), immune suppression, cardiovascular disorders (e.g., bradycardia, hypotension) chronic inflammation and/or chronic pain, sickle cell anemia, vascular wounds, and retinopathy, decreased biliary secretion, decreased pancreatic secretion, biliary spasm, and increased gastroesophageal reflux.

Compounds and compositions of the present invention may also be useful for modulation of dopamine levels for the treatment of dopamine dysregulation diseases, such as schizophrenia, attention deficit hyperactivity disorder (ADHD), attention deficit disorder (ADD), Parkinson's disease, hyperprolactinemia, depression, and addiction disorders. Thus, provided compounds and compositions may be used to treat mammals (e.g. humans) for narcotic dependence or addiction, alcohol dependence or addiction and nicotine dependence or addiction; to palliate the effects of narcotic or alcohol withdrawal, to enhance the outcomes of other narcotic or alcohol cessation therapies and to treat substance abuse and behavioral dependencies (e.g. gambling, etc.).

DETAILED DESCRIPTION OF CERTAIN EMBODIMENTS

Figure 1:
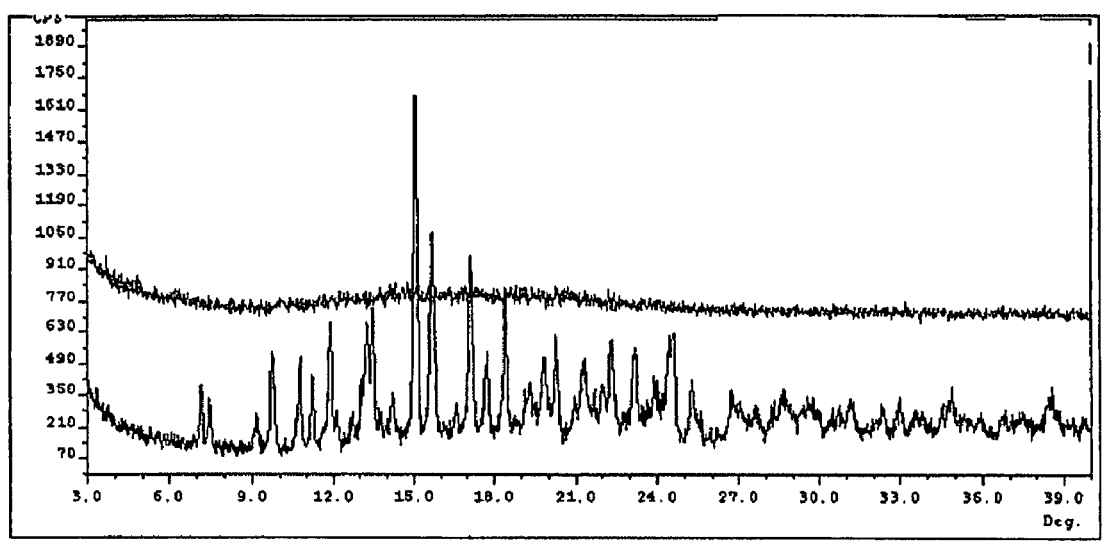
FIG. 1 depicts the X-ray diffraction pattern for Compound Ia and Compound Ia recrystallized from ethanol/water.

In certain embodiments, the present invention provides a compound of formula I:

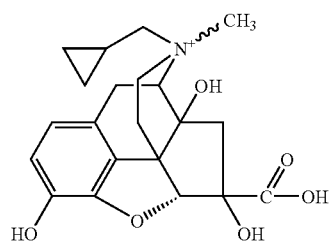

I or a pharmaceutically acceptable salt thereof.

In other embodiments, the invention provides a compound of formula IA:

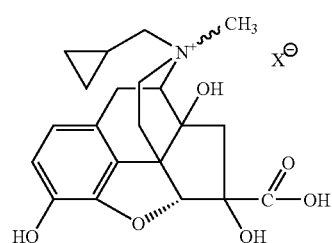

IA wherein $X^-$ is a suitable anion. One of ordinary skill in the art will appreciate that $X^-$ can be derived from a variety of organic and inorganic acids. In certain embodiments, $X^-$ is a suitable anion other than trifluoroacetate. Such anions include those derived from an inorganic acid such as hydrochloric acid, hydrobromic acid, phosphoric acid, sulfuric acid or perchloric acid. It is also contemplated that such anions include those derived from an organic acid such as acetic acid, oxalic acid, maleic acid, tartaric acid, citric acid, succinic acid, malonic acid, methanesulfonic acid, optionally substituted phenylsulfonic acids, sulfinic acid, optionally substituted phenylsulfinic acid, trifluoroacetic acid, triflic acid, optionally substituted benzoic acids, and the like. One of ordinary skill in the art will recognize that such salts are formed by other methods used in the art such as ion exchange.

Compounds of the present invention contain asymmetric carbon atoms and thus give rise to stereoisomers, including enantiomers and diastereomers. Accordingly, it is contemplated that the present invention relates to all of these stereoisomers, as well as to mixtures of the stereoisomers. Throughout this application, the name of the product of this invention, where the absolute configuration of an asymmetric center is not indicated, is intended to embrace the individual stereoisomers as well as mixtures of stereoisomers. In certain embodiments of the invention, compounds having an absolute (R) configuration are preferred. In some embodiments, provided compounds are in the (R) configuration with respect to the nitrogen.

Exemplary compounds include:

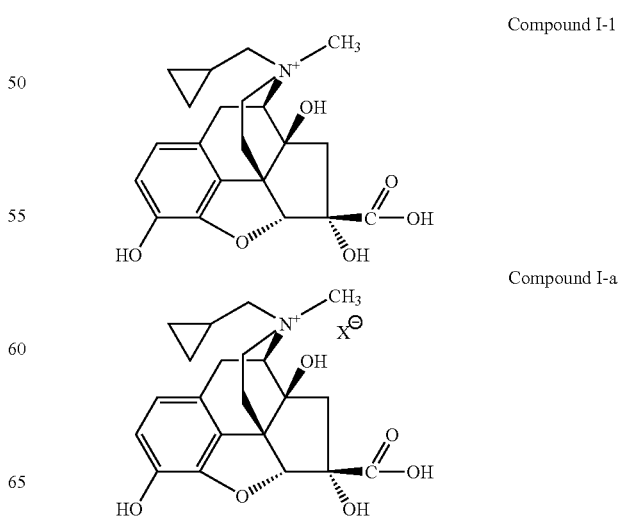

Compound I-1

Compound I-a

-continued

Compound I-b

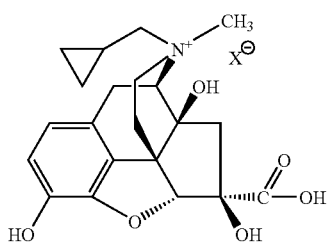

Compound I-c

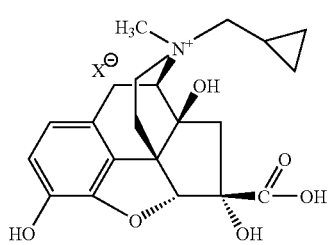

Compound I-d

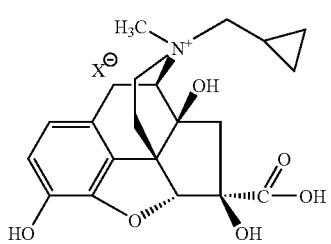

Compound I-e

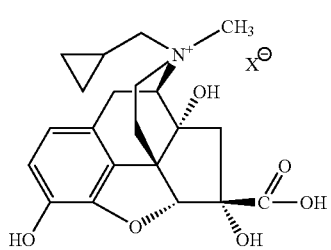

Compound I-f

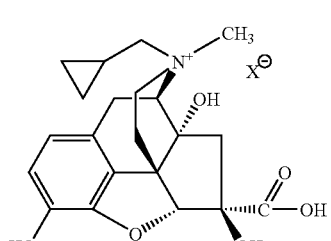

Compound I-g

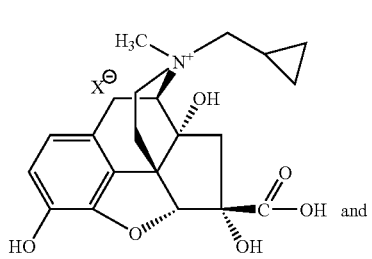

-continued

Compound I-h

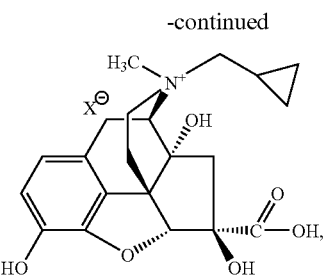

wherein each $X^-$ is a suitable anion. Alternatively or additionally, compounds I-a through I-h are provided in their free base form.

While all stereochemical isomers are depicted for compounds of formula I, it will be appreciated that mixtures of enantiomers of these formulae are accessible enriched in any stereoisomer via the present invention. In certain embodiments, a compound of formula I is provided that is enantiomerically enriched in compound Ia. As used herein, the terms "enantiomerically enriched" and "enantioenriched" denote that one enantiomer makes up at least 75% of the preparation. In certain embodiments, the terms denote that one enantiomer makes up at least 80% of the preparation. In other embodiments, the terms denote that at least 90% of the preparation is one of the enantiomers. In other embodiments, the terms denote that at least 95% of the preparation is one of the enantiomers. In still other embodiments, the terms denote that at least 97.5% of the preparation is one of the enantiomers. In yet another embodiment, the terms denote that the preparation consists of a single enantiomer to the limits of detection (also referred to as "enantiopure").

In certain embodiments, a compound of formula I is provided wherein said compound is enantiomerically enriched in compound Ia. In other embodiments, a compound of formula IA is provided wherein at least 75% of the preparation is compound Ia. In still other embodiments, a compound of formula Ia is provided wherein at least 80%, 90%, 95%, or 97.5% of the preparation is compound Ia.

Where a stereoisomer is preferred, it may, in some embodiments be provided substantially free of other stereoisomers. Thus, an stereoisomer substantially free of other stereoisomers refers to a compound which is isolated or separated via separation techniques or prepared free of the corresponding stereoisomers. According to another embodiment, the present invention provides compound Ia substantially free of other stereoisomers. "Substantially free," as used herein, means that the compound is made up of a significantly greater proportion of one stereoisomer. In certain embodiments the compound is made up of at least about 90% by weight of a preferred stereoisomer. In other embodiments of the invention, the compound is made up of at least about 99% by weight of a preferred stereoisomer. Preferred stereoisomers may be isolated from mixtures thereof by any method known to those skilled in the art, including chiral high pressure liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

Compound Ia can be prepared by any available method. In some embodiments, compound Ia is generally prepared according to Scheme I set forth below. In more particular embodiments, compound Ia can be prepared as described in Examples 2-5 herein.

As depicted in Scheme I below, compound A (methylnaltrexone) is reacted to add a suitable protecting group ("PG") at the phenolic hydroxyl, yielding compound B. Compound B then undergoes a dibromination reaction, yielding compound C. Compound C is then treated with aqueous potassium bicarbonate, to afford the diketone product, compound D.

Benzil-benzilic acid rearrangement of compound D in the presence of a strong base, such as sodium hydroxide followed by treatment with a strong acid, such as hydrochloric acid results in a contracted ring structure compound F. Finally, Mitsunobu inversion of the carboxylic acid group of compound F and displacement of a leaving group resulting from the Mitsunobu reaction provides compound Ia.

Suitable hydroxyl-protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable hydroxyl protecting groups, taken with the —OH— moiety to which it is attached, include, but are not limited to, aralkylethers, allyl ether, and the like. Examples of —OPG groups of compounds B, C and D include t-butyl ether, methyloxymethyl ether, benzoic acid ester, benzyl ether, tetrahydropyranyl ether, acetic acid ester, pivalic acid ester, t-butyldimethylsilyl ether, and the like. In certain embodiments, the —OPG group is —OC(O)CH$_3$.

When X$^-$ is the anion of an acid, compounds of formula IA may be treated with an alternate suitable acid for salt formation. Examples of solvents suitable for use in connection with preparation of alternative salt formation include polar solvents such as alkyl alcohols, such as C$_1$ to C$_4$ alcohols (e.g. ethanol, methanol, 2-propanol), water, dioxane, or THF (tetrahydrofuran) or combinations thereof. In certain embodiments, the suitable solvent is a C$_1$ to C$_4$ alcohol such as methanol, ethanol, 2-propanol, water, or combination thereof. A suitable biphasic mixture of solvents includes an aqueous solvent and a non-miscible organic solvent also can be used. Such non-miscible organic solvents are well known to one of ordinary skill in the art and include halogenated

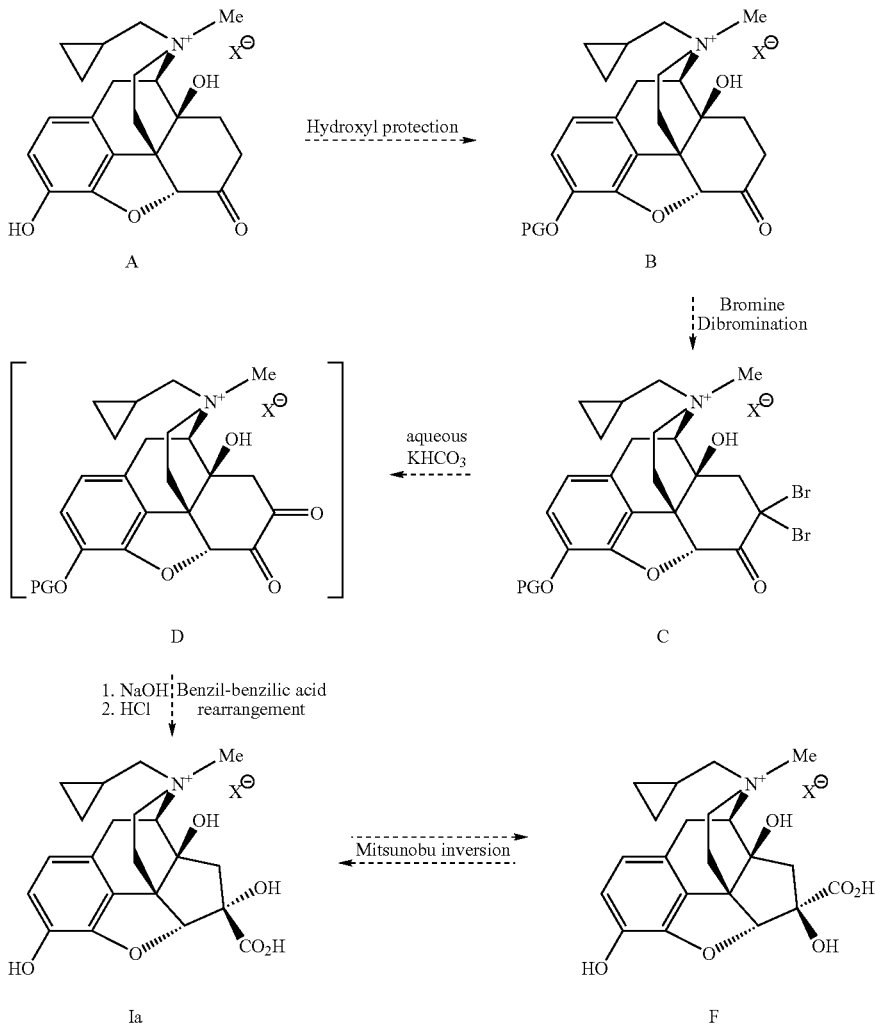

Scheme I hydrocarbon solvents (e.g. methylene chloride and chloroform), benzene and derivatives thereof (e.g. toluene), esters (e.g. ethyl acetate and isopropyl acetate), and ethers (e.g. MTBE, THF and derivatives thereof) and the like. In certain embodiments, formation of a new salt is performed in a biphasic mixture comprising water and toluene. In other embodiments, the suitable acid is water soluble such that the reaction is performed in a mixture of toluene and a suitable aqueous acid, such as aqueous hydrochloric acid.

Pharmaceutically acceptable salt(s), are those salts of compounds of the invention that are safe and effective for use in mammals and that possess the desired biological activity. Pharmaceutically acceptable salts include salts of acidic or basic groups present in compounds of the invention. Pharmaceutically acceptable acid salts include, but are not limited to, chloride, bromide, iodide, nitrate, sulfate, bisulfate, phosphate, acid phosphate, isonicotinate, acetate, lactate, salicylate, citrate, tartrate, pantothenate, bitartrate, carbonate, ascorbate, succinate, maleate, gentisinate, fumarate, gluconate, glucaronate, saccharate, formate, carboxylate, benzoate, glutamate, sulfonate, methanesulfonate, ethanesulfonate, benzensulfonate, p-toluenesulfonate, selenate, and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 J. PHARM. SCI. 1-19 (1977), incorporated herein by reference. In some embodiments, salts of use in compositions of the invention are those that have been described for methylnaltrexone, e.g., methylnaltrexone bromide, etc. However, the invention is not limited to these specific salts.

It is readily apparent that a compound of formula I contains both a quaternized nitrogen group and a carboxylate group. One of ordinary skill in the art will recognize that the carboxylate group of a compound of formula I can associate or interact with the quaternized nitrogen of a compound of formula I. Such association or interaction between two groups of a compound of formula I via an intermolecular interaction or can form between those groups of the same compound via an intramolecular interaction. The present invention contemplates both such forms.

Pharmaceutically acceptable salts of compounds of formula I can be prepared by any suitable method resulting in formation a salt. One of ordinary skill in the art will appreciate that compounds of formula I as prepared by the methods of the present invention, may be treated with a suitable acid to form a salt thereof.

For example, in some embodiments, a salt of a provided compound is formed by combining a compound of formula I and an appropriate acid. For example, compounds of formula I and hydrobromic acid can be combined in about equimolar amounts. In certain embodiments, compound Ia is treated with HBr to form the bromide salt thereof. In other embodiments, compound Ia is treated with HCl to form the chloride salt thereof. Treatment of a compound with acid is optionally carried out in a solvent in which at least one of compound Ia and HBr has at least some solubility. For example, compound Ia and HBr acid can be dissolved together in a solvent, and then solvent can be removed to yield desired salt.

Suitable solvents for forming the salts of the invention include organic solvents such as, for example, alcohols, ethers, hydrocarbons, halogenated hydrocarbons, nitrites, mixtures thereof, and the like. In some embodiments, the organic solvent is a volatile solvent such as methanol, ethanol, isopropanol, diethyl ether, pentane, hexane, benzene, dichloromethane, acetonitrile, mixtures thereof and the like. In some embodiments, the organic solvent is an alcohol such as methanol, ethanol, n-propanol, ispropanol, mixtures thereof and the like. In some embodiments, the organic solvent is ethanol.

A salt of a compound of formula IA can also be prepared by replacing the anion of a different salt of a compound of formula IA with a desired anion salt. For example, compound Ia HCl, or other compound Ia salt, can be treated with hydrobromic acid or a bromide salt to form compound Ia bromide salt. This anion-replacement reaction can be optionally carried out in a solvent, such as an organic solvent described herein.

In some embodiments, isolated compounds of formula I may be prepared as a solid form. In some embodiments, isolated compounds of formula IA may be prepared as a solid form. One of ordinary skill in the art will recognize that solid form includes various such forms including powders, particles, and the like. It will be appreciated that such solid forms can be included in, e.g., tablets, granules, etc.

In other embodiments, isolated compounds of formula I may be prepared in solution. In some embodiments, isolated compounds of formula IA may be prepared in solution.

According to one aspect, the present invention provides a method for preparing compound Ia:

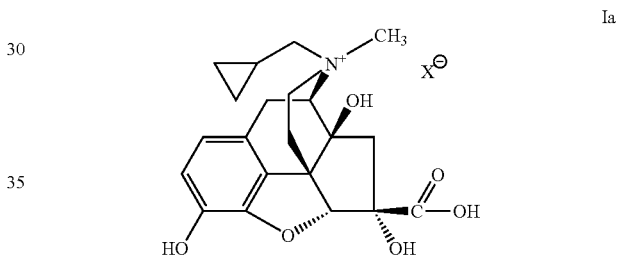

wherein X⁻ is a suitable anion, or a pharmaceutically acceptable salt thereof. In certain embodiments, the method comprises preparation of a pharmaceutically acceptable salt of compound Ia. In some embodiments, the salt is selected from the group consisting of a chloride, sulfate, bisulfate, hydroxyl, tartrate, nitrate, citrate, bitartrate, carbonate, phosphate, malate, maleate, bromide, iodide, fluoride, fumarate sulfonate, methylsulfonate, formate, carboxylate, sulfate, methylsulfate and succinate salt of compound Ia. In some embodiments, the salt is a chloride salt of compound Ia. In some embodiments, the salt is a bromide salt of Compound Ia.

Additionally provided are methods for determining the presence of a compound of formula I in a composition. In certain embodiments, methods of detection of a compound of formula I below or above a designated level are preferred. Detection of individual compound(s) in a composition by HPLC analysis and determining the presence of compound below or above a specified level are preferred. Preferred concentration levels which are not exceeded for one or more compound(s) as described herein.

Compositions, Uses, and Kits

Pharmaceutical compositions of the invention can be manufactured by methods well known in the art such as conventional granulating, mixing, dissolving, encapsulating, lyophilizing, or emulsifying processes, among others. Compositions comprising a compound of formula I may be produced in various forms, including granules, dispersions, extrusions, precipitates, or particulates, powders, including freeze dried, rotary dried or spray dried powders, amorphous powders, tablets, capsules, syrup, suppositories, injections, emulsions, elixirs, suspensions or solutions. Compositions comprising a compound of formula I may optionally contain additional excipients including, but not limited to, stabilizers, pH modifiers, surfactants, bioavailability modifiers, etc., and combinations thereof.

Pharmaceutical compositions may be prepared as liquid suspensions or solutions using a liquid, such as, but not limited to, an aqueous solution, water, an oil, an alcohol, and combinations of these. Pharmaceutically suitable surfactants, suspending agents, or emulsifying agents, may be added for oral or parenteral administration. Suspensions may include oils, such as but not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension compositions may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension compositions.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, compositions of the invention can be formulated for pharmaceutical administration to a subject. A "subject" as used herein means a mammal to whom a composition or formulation is administered, and includes human and animal subjects, such as domestic animals (e.g., horses, dogs, cats, etc.). Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, compositions are administered orally, intravenously, intramuscularly, or subcutaneously. Pharmaceutical compositions of the invention may be designed to be short-acting, fast-releasing, or long-acting. Still further, compounds can be administered in a local rather than systemic means, such as local site administration (e.g., by injection).

Sterile injectable forms of the compositions of the invention may be aqueous or oleaginous suspension. Suspensions may be formulated according to techniques known in the art using suitable dispersing or wetting agents and suspending agents. A sterile injectable preparation may also be a sterile injectable solution or suspension in a non-toxic parenterally acceptable diluent or solvent, for example as a solution in 1,3-butanediol. Among acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. Oil solutions or suspensions may also contain a long-chain alcohol diluent or dispersant, such as carboxymethyl cellulose or similar dispersing agents which are commonly used in pharmaceutical compositions, including emulsions and suspensions. Other commonly used surfactants, such as Tweens, Spans and other emulsifying agents or bioavailability enhancers which are commonly used in the manufacture of pharmaceutically acceptable solid, liquid, or other dose forms may also be used for the purposes of compositions. Compounds may be formulated for parenteral administration by injection such as by bolus injection or continuous infusion. A unit dose form for injection may be in ampoules or in multi-dose containers.

Pharmaceutical compositions of the invention may be orally administered in any orally acceptable dose form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of the invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

Pharmaceutical compositions of the invention may also be administered topically, especially when the target of treatment includes areas or organs readily accessible by topical application, including diseases of the eye, the skin, or the lower intestinal tract. Suitable topical compositions are readily prepared for each of these areas or organs.

Topical application for the lower intestinal tract may be effected in a rectal suppository composition (see above) or in a suitable enema composition. Topically-transdermal patches may also be used. For topical applications, the pharmaceutical compositions may be formulated in a suitable ointment containing the active component suspended or dissolved in one or more carriers. Carriers for topical administration of the compounds of the invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of the invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The pharmaceutical compositions of the invention preferably are formulated for administration to a subject having, or at risk of developing or experiencing a recurrence of, effects or side effects of opioid receptor activity. The term "subject", as used herein, means an animal, preferably a mammal, more preferably a human. Preferred pharmaceutical compositions of the invention are those formulated for oral, intravenous, or subcutaneous administration. However, any of the above dose forms containing a therapeutically effective amount of a compound of Formula I or an additional therapeutic agent of the invention are well within the bounds of routine experimentation and therefore, well within the scope of the instant invention.

In some embodiments, the pharmaceutical composition of the invention further comprise another pharmaceutically active agent. In some embodiments, such other pharmaceutically active agent is one that is normally administered to a subject with a disease, disorder or condition being treated. In other embodiments, such other pharmaceutically active agent is one that is administered to a subject to treat another disease, disorder or condition.

An "effective amount" or "therapeutically effective amount" of a provided compound, or pharmaceutically acceptable composition thereof, is an amount sufficient to achieve a desired therapeutic and/or prophylactic effect. For example, an "effective amount" is at least a minimal amount of a provided compound, or a pharmaceutically acceptable composition thereof, that is sufficient for preventing, ameliorating, reducing, delaying, or diminishing severity of one or more symptoms of a disorder associated with modulation of μ-, κ-, or δ-opioid receptors, and/or for preventing, ameliorating, delaying or diminishing severity of side effects associated with opioid analgesic therapy (e.g., gastrointestinal dysfunction, etc.). Alternatively or additionally, an "effective amount" of a provided compound, or pharmaceutically acceptable composition thereof, is an amount sufficient for prevention, amelioration, reduction, delay or a decrease in the symptoms associated with a disease associated with aberrant endogenous peripheral opioid or μ opioid receptor activity (e.g., idiopathic constipation, ileus, etc.). The amount of compound needed will depend on the effectiveness of the inhibitor for the given cell type and the length of lime required to treat the disorder. It should also be understood that a specific dosage and treatment regimen for any particular subject will depend upon a variety of factors, including the activity of the specific compound employed, the age, body weight, general health, sex, and diet of the subject, time of administration, rate of excretion, drug combinations, the judgment of the treating physician, and the severity of the particular disease being treated. The amount of additional therapeutic agent present in a composition of the invention typically will be no more than the amount that would normally be administered in a composition comprising that therapeutic agent as the only active agent. Preferably, the amount of additional therapeutic agent will range from about 50% to about 100% of the amount normally present in a composition comprising that agent as the only therapeutically active agent.

In another aspect, the invention provides a method for treating a subject having, or at risk of developing or experiencing a recurrence of, an opioid receptor mediated disorder. As used herein, the term "opioid receptor-mediated disorder" includes any disorder, disease or condition which is caused or characterized by an increase in opioid receptor (e.g., μ-, κ-, δ-opioid receptor) expression or activity, or which requires opioid receptor (e.g., μ-, κ-, δ-opioid receptor) activity. The term "opioid receptor-mediated disorder" also includes any disorder, disease or condition in which inhibition or antagonism of opioid receptor activity (e.g., μ-, κ-, δ-opioid receptor) is beneficial.

As discussed above, the present invention provides compounds of formula I and compositions useful in antagonizing undesirable side effects of opioid analgesic therapy (e.g., gastrointestinal effects (e.g., delayed gastric emptying, altered GI tract motility), etc.). Furthermore, provided compounds and compositions may be used to treat subjects having disease states that are ameliorated by binding μ-, κ-, and/or δ-opioid receptors, or in any treatment wherein temporary suppression of the μ-, κ-, and/or δ-opioid receptor system is desired (e.g., ileus, etc.). In certain embodiments, methods of use of provided compounds and compositions are in human subjects.

Accordingly, administration of provided compounds and compositions may be advantageous for treatment, prevention, amelioration, delay or reduction of side effects of opioid administration, such as, for example, gastrointestinal dysfunction (e.g., inhibition of intestinal mobility, constipation, GI sphincter constriction, nausea, emesis (vomiting), biliary spasm, opioid bowel dysfunction, colic), dysphoria, pruritis, urinary retention, depression of respiration, papillary constriction, cardiovascular effects, chest wall rigidity and cough suppression, depression of stress response, and immune suppression associated with use of narcotic analgesia, etc, or combinations thereof. Use of provided compositions may thus be beneficial from a quality of life standpoint for subjects receiving administration of opioids, as well as to reduce complications arising from chronic constipation, such as hemorrhoids, appetite suppression, mucosal breakdown, sepsis, colon cancer risk, and myocardial infarction.

In some embodiments, provided compounds and compositions are useful for administration to a subject receiving short term opioid administration. In some embodiments, provided compounds and compositions are useful for administration to subjects suffering from post-operative gastrointestinal dysfunction.

In other embodiments, provided compounds and compositions are also useful for administration to subjects receiving chronic opioid administration (e.g., terminally ill patients receiving opioid therapy such as an AIDS patient, a cancer patient, a cardiovascular patient; subjects receiving chronic opioid therapy for pain management; subjects receiving opioid therapy for maintenance of opioid withdrawal). In some embodiments, the subject is a subject using opioid for chronic pain management. In some embodiments, the subject is a terminally ill patient. In other embodiments the subject is a person receiving opioid withdrawal maintenance therapy.

Alternatively, additional uses for provided compounds and compositions described herein may be to treat, reduce, inhibit, or prevent effects of opioid administration including, e.g., aberrant migration or proliferation of endothelial cells (e.g., vascular endothelial cells), increased angiogenesis, and increase in lethal factor production from opportunistic infectious agents (e.g., *Pseudomonas aeruginosa*). Additional advantageous uses of provided compounds and compositions include treatment of opioid-induced immune suppression, inhibition of angiogenesis, inhibition of vascular proliferation, treatment of pain, treatment of inflammatory conditions such as inflammatory bowel syndrome, treatment of infectious diseases and diseases of the musculoskeletal system such as osteoporosis, arthritis, osteitis, periostitis, myopathies, and treatment of autoimmune diseases.

In certain embodiments, provided compounds and compositions may be used in methods for preventing, inhibiting, reducing, delaying, diminishing or treating gastrointestinal dysfunction, including, but not limited to, irritable bowel syndrome, opioid-induced bowel dysfunction, colitis, post-operative, paralytic, or postpartum ileus, nausea and/or vomiting, decreased gastric motility and emptying, inhibition of the stomach, and small and/or large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, abdominal or epigastric pain and discomfort, constipation, idiopathic constipation, post-operative gastrointestinal dysfunction following abdominal surgery (e.g., colectomy (e.g., right hemicolectomy, left hemicolectomy, transverse hemicolectomy, colectomy takedown, low anterior resection) or hernia repair), and delayed absorption of orally administered medications or nutritive substances.

Compounds of the present invention and compositions thereof are also useful in treatment of conditions including cancers involving angiogenesis, immune suppression, sickle cell anemia, vascular wounds, and retinopathy, treatment of inflammation associated disorders (e.g., irritable bowel syndrome), immune suppression, chronic inflammation.

Compounds of the present invention and compositions thereof described herein can be used to modulate dopamine levels for the treatment of dopamine dysregulation diseases. A "dopamine dysregulation disease or disorder" is meant a disease or disorder characterized or mediated by abnormal levels of dopamine in the brain. Examples of dopamine dysregulation diseases include schizophrenia, attention deficit hyperactivity disorder (ADHD), attention deficit disorder (ADD), Parkinson's disease, hyperprolactinemia, depression, Tourette's syndrome, and addiction. Methods of treating a dopamine dysregulation disorder by administering a compound of formula I or composition thereof are provided.

As used herein, addiction refers to behavior resulting from compulsive substance use and is characterized by apparent total dependency on a substance or behavior. Symptomatic of the addictive behavior is (i) overwhelming involvement with the use of a substance or activity, (ii) the securing of supply of the substance or ability to engage in the activity, and (iii) a high probability of relapse after withdrawal. Methods of treating addiction by administering a compound of formula I or composition thereof are provided.

In still further embodiments, veterinary applications (e.g., treatment of domestic animals, e.g. horse, dogs, cats, etc.) of use of compositions are provided. Thus, use of provided compositions in veterinary applications analogous to those discussed above for human subjects is contemplated. For example, inhibition of equine gastrointestinal motility, such as colic and constipation, may be fatal to a horse. Resulting pain suffered by the horse with colic can result in a death-inducing shock, while a long-term case of constipation may also cause a horse's death. Treatment of equines with peripheral opioid antagonists has been described, e.g., in U.S. Patent Publication No. 20050124657 published Jan. 20, 2005.

It will also be appreciated that provided compounds and compositions can be employed in combination therapies, that is, a compound of formula I and compositions thereof, can be administered concurrently with, prior to, or subsequent to, one or more other desired therapeutics or medical procedures. Particular combination therapies (therapeutics or procedures) to employ in a combination regimen will take into account compatibility of the desired therapeutics and/or procedures and the desired therapeutic effect to be achieved. It will also be appreciated that therapies employed may achieve a desired effect for the same disorder (for example, a compositions may be administered concurrently with another compound used to treat the same disorder), or they may achieve different effects (e.g., control of any adverse effects). As used herein, additional therapeutic compounds which are normally administered to treat or prevent a particular disease, or condition, are known as "appropriate for the disease, or condition, being treated".

In some embodiments where a compound of formula I is present in pharmaceutical compositions, the amount of the compound comprises from about 0.30 wt % to about 99.0 wt %. In some embodiments where a compound of formula I is present in pharmaceutical compositions, the amount of the compound comprises at least 5% of total active compound contained in the composition. In some embodiments, the compound comprises at least about 10% of total active compound, at least 20% of total active compound, at least 50% of total active compound, at least 75% of total active compound, at least 90% of total active compound, at least 95% of total active compound, at least 99% of total active compound, or more in a composition.

In some embodiments, provided compositions include one or more other active compounds in addition to compounds of the present invention. In some embodiments, compositions comprise a provided compound and an additional opioid receptor antagonist (e.g., a µ-, κ-, δ-opioid receptor antagonist). In certain embodiments, compositions comprise methylnaltrexone or a pharmaceutically active salt thereof.

In some embodiments, compositions comprise both an opioid and an opioid receptor antagonist (e.g., a µ-, κ-, δ-opioid receptor antagonist). Such combination products, containing both an opioid and an antagonist, would allow simultaneous relief of pain and minimization of opioid-associated side effects (e.g., gastrointestinal effects (e.g., delayed gastric emptying, altered GI tract motility), etc.).

Opioids useful in treatment of analgesia are known in the art. For example, opioid compounds include, but are not limited to, alfentanil, anileridine, asimadoline, bremazocine, burprenorphine, butorphanol, codeine, dezocine, diacetylmorphine (heroin), dihydrocodeine, diphenoxylate, ethylmorphine, fedotozine, fentanyl, funaltrexamine, hydrocodone, hydromorphone, levallorphan, levomethadyl acetate, levorphanol, loperamide, meperidine (pethidine), methadone, morphine, morphine-6-glucoronide, nalbuphine, nalorphine, nicomorphine, opium, oxycodone, oxymorphone, papaveretum, pentazocine, propiram, propoxyphene, remifentanyl, sufentanil, tilidine, trimebutine, and tramadol. In some embodiments the opioid is at least one opioid selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, nicomorphine, oxycodone, oxymorphone, papaveretum, pentazocine, propiram, propoxyphene, sufentanil and/or tramadol. In certain embodiments, the opioid is selected from morphine, codeine, oxycodone, hydrocodone, dihydrocodeine, propoxyphene, fentanyl, tramadol, and mixtures thereof. In a particular embodiment, the opioid is loperamide. In another particular embodiment, the opioid is hydromorphone. In other embodiments, the opioid is a mixed agonist such as butorphanol. In some embodiments, the subjects are administered more than one opioid, for example, morphine and heroin or methadone and heroin.

The amount of additional active compound(s) present in combination compositions of the invention will typically be no more than the amount that would normally be administered in a composition comprising that active compound as the only therapeutic agent. In certain embodiments, the amount of additional active compound will range from about 50% to 100% of the amount normally present in a composition comprising that compound as the only therapeutic agent.

In certain embodiments, provided compounds and compositions may also be used in conjunction with and/or in combination with conventional therapies for dopamine dysregulation disorders, cancers, immune suppression, inflammatory disorders, and/or dependence or addiction disorders. For example, conventional therapies include, but may not be limited to antidepressants, stimulants and/or other compounds useful in treatment of affective disorders such as schizophrenia, depression, ADHD, ADD, Parkinson's disorder, and addiction disorders. In still other embodiments, compositions may be used in conjunction with behavioral therapy useful in treatment of such disorders.

In certain embodiments, provided compounds and compositions may also be used in conjunction with and/or in combination with conventional therapies for gastrointestinal dysfunction to aid in the amelioration of constipation and bowel dysfunction. For example, conventional therapies include, but may not be limited to functional stimulation of the intestinal tract, stool softening agents, laxatives (e.g., diphelymethane laxatives, cathartic laxatives, osmotic laxatives, saline laxatives, etc), bulk forming agents and laxatives, lubricants, intravenous hydration, and nasogastric decompression.

In other embodiments, compounds of the present invention and compositions thereof are useful in preparation of medicaments, including, but not limited to medicaments useful in the treatment of side effects of opioid administration (e.g., gastrointestinal side effects (e.g., inhibition of intestinal motility, GI sphincter constriction, constipation nausea, emesis (vomiting)), dysphoria, pruritis, etc.) or a combination thereof. Compounds and compositions of the present invention are useful for preparations of medicaments, useful in treatment of patients receiving short term opioid therapy (e.g., patients suffering from post-operative gastrointestinal dysfunction receiving short term opioid administration) or subjects using opioids chronically (e.g., terminally ill patients receiving opioid therapy such as an AIDS patient, a cancer patient, a cardiovascular patient; subjects receiving chronic opioid therapy for pain management; or subjects receiving opioid therapy for maintenance of opioid withdrawal). Still further, preparation of medicaments useful in the treatment of pain, treatment of inflammatory conditions such as inflammatory bowel syndrome, treatment of infectious diseases, treatment of diseases of the musculoskeletal system such as osteoporosis, arthritis, osteitis, periostitis, myopathies, treatment of autoimmune diseases and immune suppression, therapy of post-operative gastrointestinal dysfunction following abdominal surgery (e.g., colectomy (e.g., right hemicolectomy, left hemicolectomy, transverse hemicolectomy, colectomy takedown, low anterior resection), idiopathic constipation, and ileus (e.g., post-operative ileus, paralytic ileus, post-partum ileus), and treatment of disorders such as cancers involving angiogenesis, chronic inflammation and/or chronic pain, sickle cell anemia, vascular wounds, and retinopathy.

Still further encompassed by the invention are pharmaceutical packs and/or kits. Pharmaceutical packs and/or kits provided may comprise a provided compounds and compositions and a container (e.g., a vial, ampoule, bottle, syringe, and/or dispenser package, or other suitable container). Optionally, instructions for use are additionally provided in such kits of the invention. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with additional therapy.

In order that the invention be more fully understood, the following preparative and testing examples are set forth. These examples illustrate how to make or test specific compounds, and are not to be construed as limiting the scope of the invention in any way.

EXEMPLIFICATION

Example 1

Identification and Characterization

Previously, at least three degradation products of methylnaltrexone were demonstrated from HPLC analysis in 20 mg/mL isotonic saline solution (identified as RRT peaks at about 0.72, 0.89, and 1.48 when products were analyzed by HPLC). See, e.g., U.S. Patent Application Publication No. 20040266806, published Dec. 30, 2004. We examined 20 mg/mL saline methylnaltrexone solutions for production of degradants, and identification of degradants, as well as identification of inhibitors of formation of different degradant products. We have identified and characterized degradants which accumulate in certain methylnaltrexone solutions. In these degradation experiments, and in the formulations prepared in the examples, (R)—N-methylnaltrexone was used having less than 0.15 weight percent (S)—N-methylnaltrexone.

For HPLC analysis a Prodigy ODS-3 15 cm×2.0 mm, 3 µm particles (Phenomenex) HPLC column at a flow rate of 0.25 mL/min, using the following eluent:

| | |
|---|---|
| Mobile Phase: | Strength (Isocratic: 75:25 (v/v) 0.1% TFA in Water/Methanol |
| | Purity: (Gradient): |
| | Mobile Phase A = 95:5 (v/v) 0.1% TFA in Water/Methanol |
| | Mobile Phase B = 35:65 (v/v) 0.1% TFA in Water/Methanol |
| | Time |
| | (Min)   % Mobile Phase A |
| Gradient Program: | 0         100 |
| | 45        50 |
| | 45.1      100 |
| | 60        100 |
| Column Temperature: | 50° C. |
| Flow: | 0.25 mL/minute |
| Detection: | UV, 280 nm |
| Injection: | Strength: 5 µL |
| Purity: | 20 µL |
| Sample Solvent: | 0.05M Dibasic Sodium Phosphate pH 6.8 |

The following standards of compounds and known impurities were identified with associated calculated relative retention times:

|                              |          |
|------------------------------|----------|
| Methylnaltrexone bromide     | RRT 1.00 |
| Naltrexone base              | RRT 1.17 |
| S-Methylnaltrexone           | RRT 0.89 |
| 8-Ketomethylnaltrexone bromide | RRT 0.49 |
| Aldol dimer                  | RRT 1.77 |
| O-Methyl methylnaltrexone    | RRT 1.66 |
| 2,2,bis-methylnaltrexone     | RRT 1.55 |

Naltrexone base, S-methylnaltrexone, and O-methyl methylnaltrexone (also referred to as 3-methoxy naltrexone methobromide) are each compounds found in initial production samples. Additional impurities/degradants formed and identified include 8-ketomethylnaltrexone bromide (RRT 0.49), the aldol dimer (RRT 1.77), O-methyl methylnaltrexone (RRT 1.66), and the 2,2 bis-methylnaltrexone (RRT 1.55), as well as additional degradants resulting at relative retention time of 0.67, 0.79 and 2.26.

Each of the three additional degradants were identified by NMR analysis following isolation from column eluates, and further characterized as described herein. We found the 0.79 degradant is a novel isolated compound, identified as a ring contracted form of (R)—N-methylnaltrexone: ((3R,4R,4aS,6aR,11bS)-6-carboxy-3-(cyclopropylmethyl)-4-a,6,8-trihydroxy-3-methyl-1,2,3,4,4a,5,6,6a-octahydro-4,11-methano[1]benzofuro[3',2':2,3]cyclopenta[1,2-c]pyridin-3-ium). Thus, the present invention provides a compound of formula Ia, wherein said compound is substantially free of methylnaltrexone. Additional description of the NMR and MS data analysis which led to the identification of compound Ia is further described in A and B below.

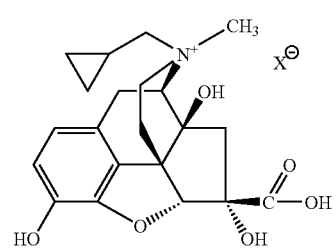

Ia

A. $^1$H and $^{13}$C NMR Analysis:

The structure of compound Ia was elucidated by interpretation of 1D and 2D NMR data ($^1$H, $^{13}$C NMR, COSY, HSQC, HMBC, TOCSY, ROESY). The $^1$H NMR spectrum in D$_2$O showed all proton signals of methylnaltrexone except for the 4 exchangeable hydroxyl and carboxylic protons (see Scheme A: Numbering System of methylnaltrexone Compound Ia). This numbering system is utilized for analytical method designation herein, and does not reflect IUPAC nomenclature designations.

Scheme A: numbering system of (R)-N-methylnaltrexone and Compound Ia

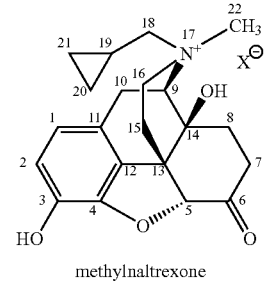

methylnaltrexone

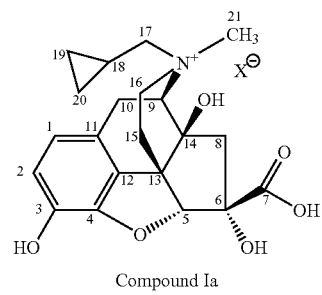

Compound Ia

By comparison, it was evident that the spectrum of compound Ia did not show the signals at δ 2.31 and 2.8-3.2, which was assigned to the C-7 methylene protons (H-7b and H-7a) of the parent compound (R)—N-methylnaltrexone. The loss of the C-7 methylene protons was further supported by the appearance of a pair of sharp doublets at δ 2.49 and 1.64 with coupling constant of 14.2 Hz, assigned to H-8a and H-8b at δ 2.49 and 1.64, respectively. These two proton signals were strongly coupled to each other in the COSY spectrum but exhibited no further spin-spin coupling to any other protons. This evidence indicated that H-8a and H-8b were flanked by two quaternary carbons with no adjacent H-7a and H-7b protons. In the HSQC spectrum, both H-8a and H-8b were correlated to a carbon resonance at δ 50.4, typical chemical shift for C-8 type methylene carbon. Detailed analysis of the HMBC spectrum revealed that both H-8a and H-8b showed two-bond correlations to C-6 at δ 80.6 and to C-14 at δ 77.3, typical oxygenated quaternary carbons, and three-bond correlations to C-7 at δ 180.4, assigned to the carboxylic group C-7. Additional three-bond correlations observed from H-8a δ 2.49 to C-5 at δ 92.3 and C-13 at δ 54.8 suggested H-8 was in a pseudo equatorial orientation, which required H-8a upface. A network of HMBC correlations such as H-5 at δ 5.03 to C-6, C-7, C-8, C-4, C-12, and C-15, plus with assistance of other 2-D experiments of COSY, HSQC, and TOCSY, completed the structure assignments for compound Ia as shown in Scheme B below. The $^1$H and $^{13}$C NMR chemical shifts were recorded from 1D NMR experiments and referenced to normal methanol signals at δ 3.35 and 49.15 for proton and carbon, respectively.

Scheme B: 1H and 13C NMR chemical shifts of Compound Ia

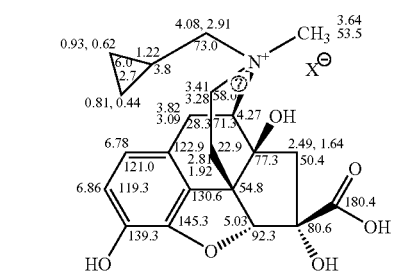

NMR data in D$_2$O/ref. MeOH ($^1$H: d 3.35; $^{13}$C: d 49.15)
C$_{21}$H$_{25}$NO$_6$$^+$/Exact Mass: 388.1755

The orientation of the carboxylic group (attached to C-6) was determined to be up on the basis of ROESY data and three-bond HMBC correlations (see Scheme C below). The ROESY data demonstrated that H-10$_{eq}$ at δ 3.82 was in β-orientation (up-face) as it was coupled to H-17 at δ 4.08. The α-oriented proton H-10$_{ax}$ at δ 3.09 was correlated to H-8b at δ 1.64, indicating H-8b was in the same face of H-10$_{ax}$. The proton H-8b showed strong HMBC coupling to the carboxylic carbon C7, revealing the anti coplanar relationship.

Scheme C: Orientation of Carboylic Group was determined by ROESY and HMBC.

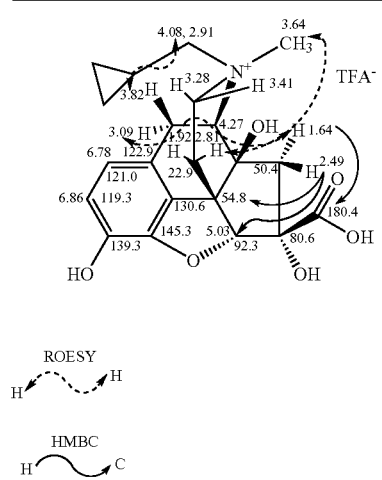

B. Mass Spectrum Analysis:

MS spectrum showed the molecular ion of m/z 388 and the unique fragment of m/z 344 due to losing a CO$_2$ group, revealing the presence of the carboxylic moiety. The measured accurate mass by adding two internal standards was 388.1750, corresponding to an ionic formula of C$_{21}$H$_{26}$NO$_6$ with experimental error of −0.4 mDa (~1.0 ppm). MS/MS spectrum of m/z 388 peak was identical to the previous observed compound Ia peak in the methylnaltrexone-saline sample. The fragmentation pattern is shown in Scheme D below.

Scheme D: MS-MS fragmentation pattern of Compound Ia

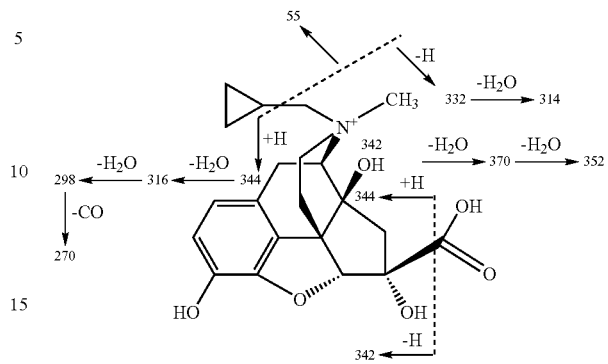

C. X-ray Crystallography Analysis:

Compound I-1 was recrystallized from ethanol/water by the following method. 30.5 mg of Compound I-1 was dissolved at about 70° C. in a solution of 2 mL of ethanol and 0.5 mL of water. The resulting solution was allowed to cool to room temperature with the aid of nitrogen gas. The resulting crystals were collected and dried overnight under vacuum at 40° C. and subjected to X-ray powder diffraction analysis. The observed X-ray diffraction peaks at 2 degrees theta are set forth in Table 1, below. The X-ray diffraction pattern as compared with amorphous compound is depicted in FIG. 1.

TABLE 1

Observed X-ray Diffraction Peaks for Compound Ia Recrystallized from Ethanol

| Angle 2-Theta (degree) | d Value Angstroms |
| --- | --- |
| 7.19 | 9.01 |
| 7.49 | 11.78 |
| 9.14 | 9.63 |
| 9.81 | 9.00 |
| 10.85 | 8.14 |
| 11.25 | 7.85 |
| 11.94 | 7.40 |
| 13.33 | 6.68 |
| 13.47 | 6.56 |
| 14.21 | 6.22 |
| 15.05 | 5.88 |
| 15.96 | 5.64 |
| 17.12 | 5.17 |
| 17.77 | 4.98 |
| 18.46 | 4.80 |
| 19.84 | 4.47 |
| 20.29 | 4.37 |
| 21.32 | 4.16 |
| 22.36 | 3.97 |
| 23.20 | 3.83 |
| 24.68 | 3.60 |

D. UV Spectra

Figure 2:
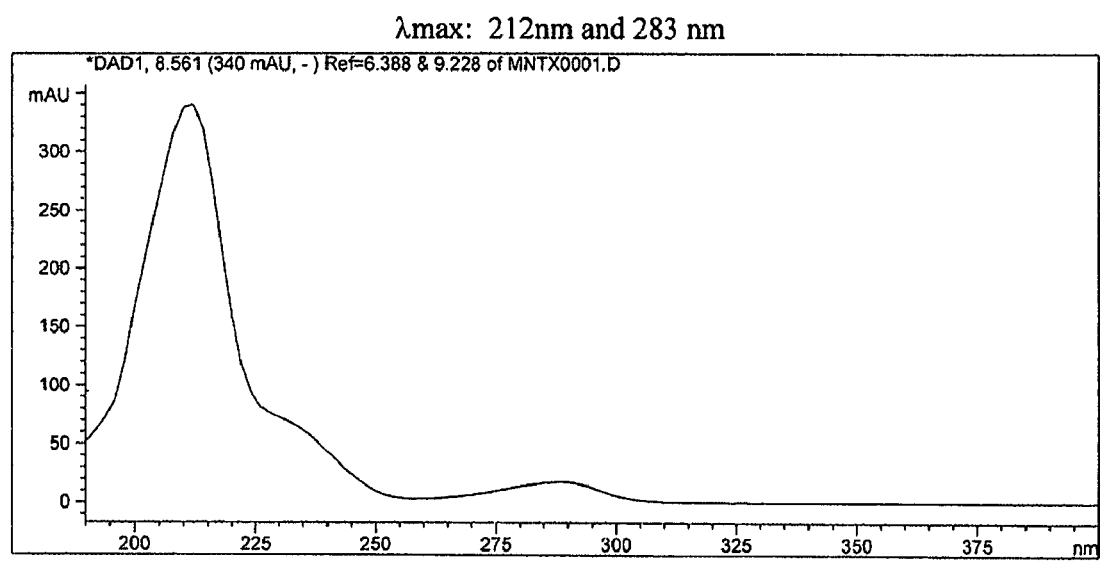
FIG. 2 depicts the UV spectrum for Compound Ia.

The UV spectrum for compound I-1 is depicted in FIG. 2.

E. Partition Coefficient

The partition coefficient of Compound I-1 was determined by the following method.

1. 20.131 mg of Compound I-1 was dissolved in 2 mL of water saturated with 1-octanol.
2. 2 mL of 1-octanol saturated with water was added to the solution from step 1.
3. The two layers were shaken over night at room temperature.

4. The two layers were analyzed for the concentration of Compound I-1.

The results of the partition coefficient determination are set forth in Table 2.

TABLE 2

| Partition Coefficient of Compound I-1. | |
|---|---|
| Partition Coefficient (P) | 0.007126 |
| Log P | −2.147 (pH: 2.2) |

F. pKa (Calculated):
According to "CompuDrugpKalc" soft ware program.
2.97 (carboxylic acid)
11.29 (phenol)
G. Aqueous Solubility:
>56 mg/ml (pH: 2.2) by adding certain additive amounts of I-1 to 1 ml of water.

Example 2

Preparation of Compound Ia (Method A)

Methylnaltrexone (20 mg/mL) in 0.4 mg/mL of Ca EDTA, 0.65% NaCl, aqueous solution was heated at 70° C. for 1 week. Resulting solution was separated by HPLC analysis as described in Example 1 above, yielding 1.55% of Compound Ia, RRT 0.79.

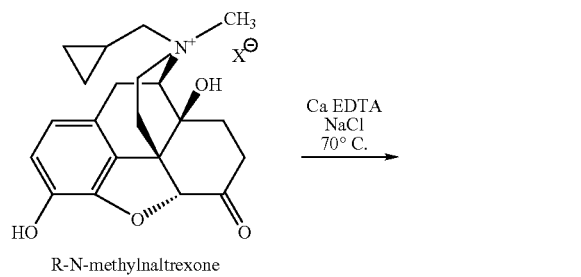

Example 3

Preparation of Compound Ia (Method B)

Lyophilized methylnaltrexone was reconstituted with 10.6 mL of normal saline, to yield a concentration of 0.8 mg/mL of methylnaltrexone in a stoppered vial. A 13 mm S2-F451 RS D 777-1 RB2 bromobutyl stopper (Dalkyo Seiko, Ltd) was removed from the vial, cut in to 4 pieces then placed back into the specified vial. The vial containing solution and stopper was then re-sealed with a stopper, and maintained at 40° C. for 6 hours. Resulting solution was separated by HPLC analysis as described in Example 1 above, yielding 2.13% of Compound Ia, RRT 0.79.

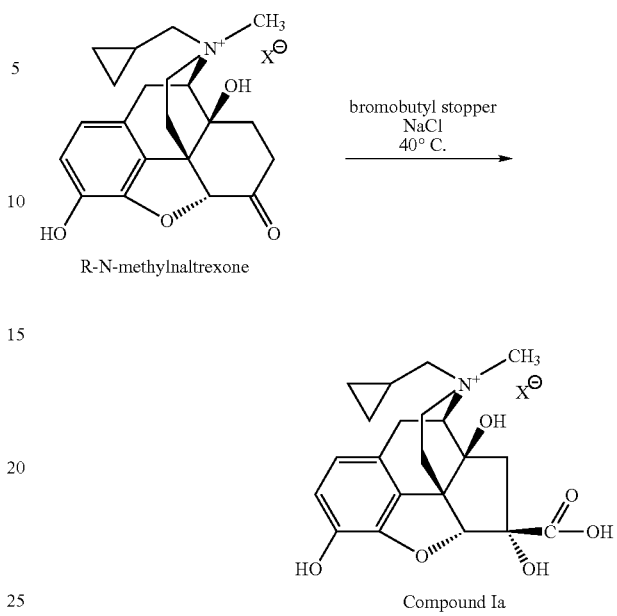

Example 4

Preparation of Compound Ia (Method C)

SeO$_2$ (9.00 g, 81.1 mmol) was added to an aqueous solution of methylnaltrexone (17.50 g, 40.1 mmole in 360 mL) then heated to 97° C. with stirring until nearly all methylnaltrexone was consumed. Given reaction mixture was cooled to ambient temperature and solid precipitates were filtered. The filter cake was washed with water and the wash filtrates were combined with the reaction filtrate. NaOH (4.8 g, 120 mmol) was added to the combined filtrates and stirred at ambient temperature until the reaction was complete. The reaction mixture was concentrated then poured into a large volume of THF under agitation. The resulting solids were partition into methanol, separated from the THF layer, concentrated, poured into a large volume of Acetone under agitation, and filtered. The filtrate was concentrated, diluted with acetone, then concentrated again several more times. The final dilution was concentrated to dryness to afford a yellow solid which was washed with acetone yielding 4.8 g of Compound Ia (30% yield).

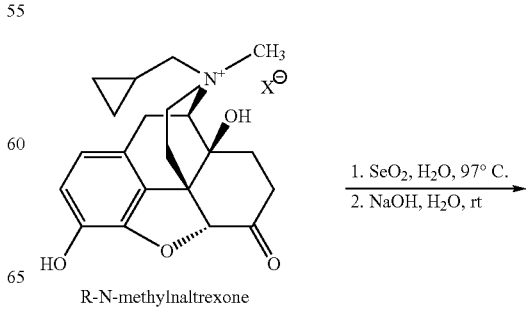

-continued

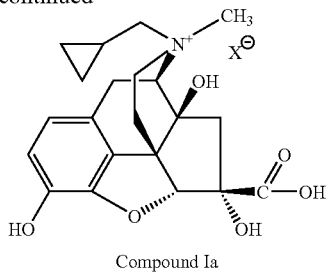

Compound Ia

Example 5

Preparation of Compound Ia (Method D)

Methylnaltrexone (2.079 g) was dissolved in 2 L of 0.2M phosphate buffer pH 7.18. The resulting colorless solution was kept at 60° C. for 114 days. The resulting solution was separated by HPLC using the following HPLC method yielding 41% of Compound Ia, RRT 0.79.

| Column: | Inertsil ODS-3 150 × 4.6 mm, 5 μm |  |  |
|---|---|---|---|
| Flow rate: | 1.5 mL/min |  |  |
| Detection: | UV at 280 nm |  |  |
| Column temp. | 50° C. |  |  |
| Inj Volume: | 20 μl |  |  |
| Mobile phase: | A Water:Methanol:Trifluoroacetic acid (95:5:0.1% v/v/v) |  |  |
|  | B Water:Methanol:Trifluoroacetic acid (35:65:0.1% v/v/v) |  |  |
|  | Time | % A | % B |
| Gradient: | 0 | 100 | 0 |
|  | 45 | 50 | 50 |
|  | 45.1 | 100 | 0 |
|  | 50 | 100 | 0 |

Example 6

Biological Activity Assays

A. Radioligand Receptor Binding Assays

Compounds can be characterized in radioligand receptor binding assays, using ligands that are specific for the mu, delta and kappa receptors. Binding assays may utilize guinea pig brain membranes, human 293 cells, or stably transfected Chinese Hamster Ovary (CHO) cells expressing each of the three opioid receptors. Such assays are known in the art, and have been described, for example, in Martin, et al., J. Pharm. Exp. Ther., 301, 661-671 (2003); Zaki, et al., J. Pharm. Exp. Ther., 298, 1015-1020 (2002); Wentland, et al., J. Med. Chem., 46, 838-849 (2003) and Neumeyer, et al., J. Med. Chem. 43:114 (2000).

For example, membranes can be isolated from CHO cells that stably express either the human mu, delta or kappa opioid receptor. At approximately 80% confluence, cells are harvested using a cell scraper. Cells and media from plates are centrifuged at 200×g for 10 min at 4° C., then resuspended in 50 mM Tris-HCl, pH 7.5. Cells are then homogenized by use of a Polytron; centrifuged at 48,000×g for 20 min at 4° C., then resuspended in 50 mM Tris-HCl, pH 7.5, at an estimated final protein concentration of 5-10 mg/ml, as determined by the Bradford method. Prepared membranes may be stored, at −80° C. until use. Alternatively, guinea pig brain membranes can be prepared and used as previously described in Neumeyer, et al., J. Med. Chem. 43:114 (2000).

For assays, cell membranes are incubated at 25° C. with radiolabeled ligand in a final volume of 1 ml of 50 mM Tris-HCl, pH 7.5. Ligands for each of mu, kappa, and delta are known in the art. Any suitable ligand may be used, including, for example, a mu-selective peptide (e.g., DAMGO) may be selected for use in assays, as well as a kappa selective ligand (e.g., U69,593), and a delta selective ligand (e.g., naltrindole). Incubation times of about 60 minutes are used for the mu-selective peptide [$^3$H]DAMGO and the kappa-selective ligand [$^3$H]U69,593, and about 4 hours of incubation for the delta-selective antagonist [$^3$H]naltrindole. Nonspecific binding is measured by inclusion of a non-selective ligand (e.g., 1 μM naloxone). Binding can be terminated by filtering the samples through filters and washing filters. For example, binding assays may be passed through Schleicher & Scheull No. 32 glass fiber filters using a Brandel 48-well cell harvester. Filters are subsequently washed three times with 3 ml of cold 50 mM Tris-HCl, pH 7.5, and can be counted in 2 ml of Ecoscint A scintillation fluid. For [$^3$H]U69,593 binding, filters are soaked in 0.1% polyethylenimine for at least 30 minutes before use.

$IC_{50}$ values can be calculated by a least squares fit to a logarithm-probit analysis. $K_i$ values of unlabeled compounds are calculated from the equation $K_i=(IC.sub.50)/1+S$ where S=(concentration of radioligand) ($K_d$ of radioligand). Cheng and Prusoff, Biochem. Pharmacol. 22:3099 (1973).

B. $^{35}$S GTPγS Binding Assays.

Membranes from CHO cell lines expressing either mu, delta or kappa receptor, are incubated with various concentrations of each opioid for 60 minutes at 30° C. in a final volume of 0.5 ml of assay buffer (50 mM Tris-HCl, 3 mM MgCl.sub.2, 0.2 mM EGTA, 100 mM NaCl, pH 7.5) containing 3 μM GDP and 0.08 nM $^{35}$S GTPγS. Basal binding activity can be determined in the presence of GDP and the absence of opioids; and nonspecific binding can be determined by including 10 μM unlabeled $^{35}$S GTPγS. Incubation can be terminated by filtration under vacuum through glass fiber filters, followed by washes with 3 ml ice-cold 50 mM Tris-HCl, pH 7.5. Samples can be allowed to equilibrate overnight and counted in 2 ml Ecoscint A scintillation fluid for 2 minutes in a liquid scintillation counter.

For $^{35}$S GTPγS binding assays, percent stimulation of $^{35}$S GTPγS binding is defined as [(opioid-stimulated binding-basal binding) basal binding]×100% stimulation is plotted as a function of opioid concentration (log scale). $EC_{50}$ and Emax values are determined by linear regression analysis. All data may be compared across conditions using, for example, ANOVA and non-paired two-tailed Student's tests.

C. Tail Flick Assay.

The thermal nociceptive stimulus can be 55° C. water with the latency to tail flick or withdrawal taken as the endpoint. McLaughlin et al., J. Pharmacol. Exp. Ther. 289:304 (1999); McLaughlin et al., Eur. J. Pharmacol. 320:121 (1997); Neumeyer, et al., J. Med. Chem. 43:114 (2000); and Xu et al., J. Pharmacol. Exp. Ther. 279:539 (1996). Intracerebroventricular (i.c.v.) injections are made directly into the lateral ventricle. A mouse is lightly anesthetized with ether, an incision is made in the scalp, and the injection is made 2 mm lateral and 2 mm caudal to bregma at a depth of 3 mm using a 10 μl Hamilton microliter syringe. The volume of all i.c.v. injections are about 5 μl. After determining control latencies, the mouse receives graded i.c.v. doses of opioid agonists or antagonists at various times. When measuring agonist activity, selective antagonists, .beta.-FNA (mu), ICI 174,864 (delta) and/or -BNI (kappa) can be used as previously described. McLaughlin et al., J. Pharmacol. Exp. Ther. 289: 304 (1999). When measuring antagonist activity, morphine, DPDPE, and U50,488 are co-administered with the new compounds as a single i.c.v. injection, with testing taking place 20 mm after the injection. A cut-off time of 15 seconds is used; if the mouse fails to display a tail flick, the tail is removed from the water and that animal can be assigned a maximal antinociceptive score of 100%. Mice showing no response within 5 seconds in the initial control test are eliminated from the experiment. Antinociception at each time point can be calculated according to the following formula: % antinociception=100×(test latency-control latency)/(15-control latency).

Antagonist activity can be determined by calculating the $pA_2$ values for a compound. For example, a morphine dose-response curve is generated. Then morphine and antagonist is co-injected and the morphine dose-response curve is generated in the presence of varying doses of the antagonist. The tail flick test can be used to characterize both mu and delta opioid receptor agonist and antagonist activity.

D. Writing Assay.

Because antinociception induced by kappa opioid agonists has been difficult to evaluate in the tail flick test, the action of the compounds can be determined in the mouse acetic-acid writhing test. After receiving i.c.v. doses of opioid agonists and antagonists at various times, an i.p. injection of 0.6% acetic acid (10 ml/kg) are administered to each mouse. Five minutes after administration, the number of writhing signs displayed by each mouse are counted for an additional 5 minutes. Antinociception for each tested mouse can be calculated by comparing the test group to a control group in which mice were treated with i.c.v. vehicle solution.

E. Neurotransmitter Assay

Figure 3:
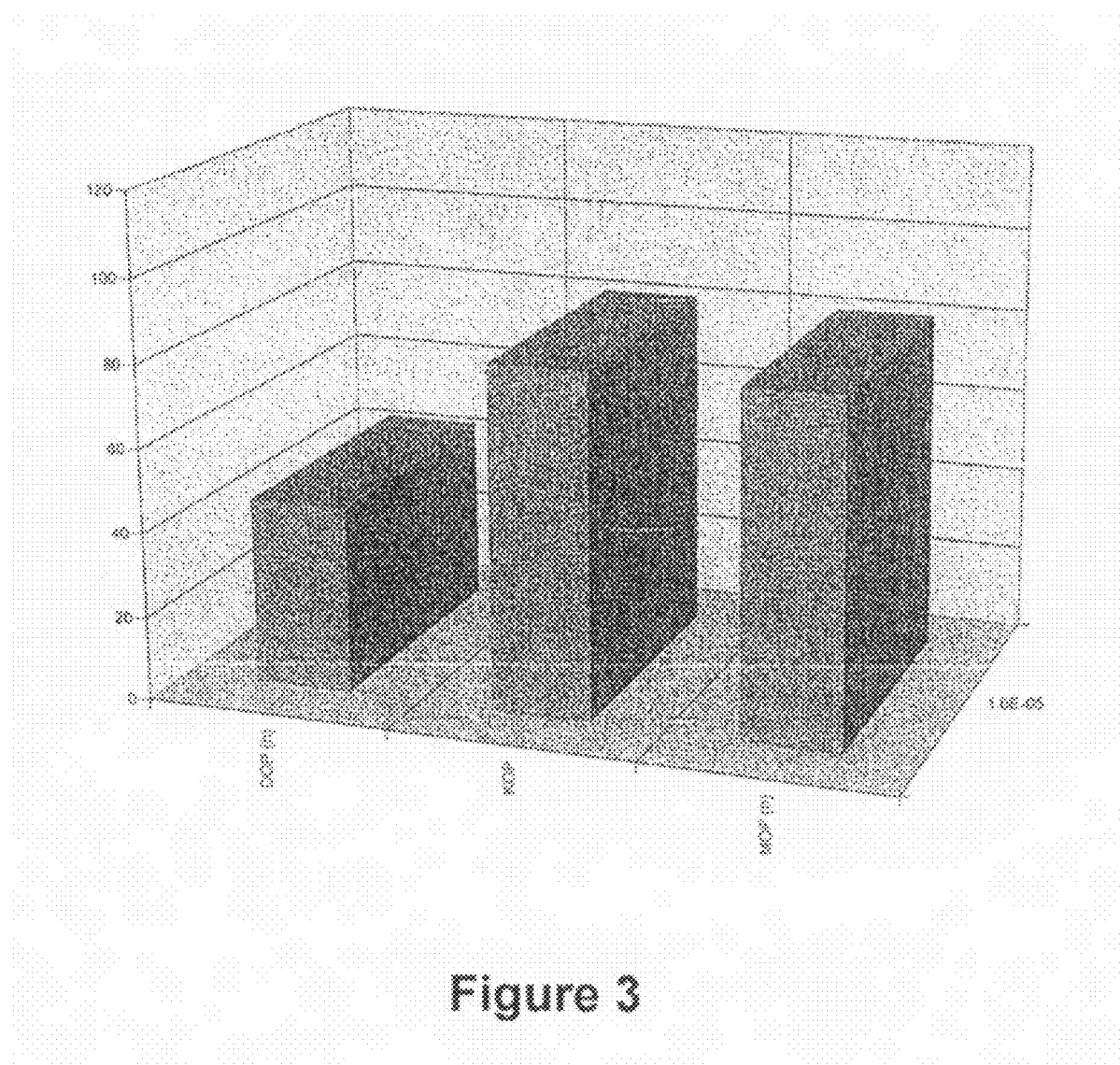
FIG. 3 depict results from the neurotransmitter assay for Compound Ia.

Results from the neurotransmitter assay for Compound Ia are set forth in Table 3 and depicted in FIG. 3.

TABLE 3

Neurotransmitter Assay Results for Compound Ia

| Receptor | Percent Inhibition (Average; N = 2) | Radioligand | Kd (M) | Reference Agent | Ki (M) of Reference Agent |
|---|---|---|---|---|---|
| Delta 2 (h) | 44.47% | [3H]-Naltrindole | 3E-10 | Naltriben | 6.54E-10 |
| Kappa 1 | 82.09% | [3H]U-69593 | 0.25E-9 | U-69593 | 2.97E-10 |
| Mu (h) | 81.62% | [3H]-Diprenorphine | 2E-10 | Naloxone HCL | 3.71E-9 |

F. Opioid Functional Antagonist Assay

The opioid functional antagonist assay was performed as described in Coward P, Chan S D, Wada H G, Humphries G M, Conklin B R. (1999) and Chimeric G proteins allow a high-throughput signaling assay of G-coupled receptors. *An. Biochem.* 270(2): 242-8 (1999). Specifically, the assay was performed as follows.

1. Cells were grown to confluence in 96-well plates, washed physiological buffer was added before analysis.
2. Cells were loaded with dye that measures intracellular calcium.
3. Agent or CTOP was added to cells.
4. fluorescence was measured at 485 nm excitation/525 nm emission every 3 seconds for at least 20 seconds.
5. Cells were activated using 10 nM DAMGO agonist.
6. Fluorescence was measured for 60 seconds more.

The cells used were CHO cells that express human recombinant Mu opioid receptors, DAMGO agonist is a peptide with the amino acid sequence Tyr-D-Ala-Gly-N-methyl-Phe-Gly-ol, and CTOP is a peptide with the amino acid sequence D-Phe-Cys-Tyr-D-Trp-Orn-Thr-Pen-Thr amide (disulfide bridge 2-7).

The opioid functional antagonist assay is characterized as measuring calcium levels where 0% (basal) was 350 nM calcium and 100% (maximum, 10 nM DAMGO) was 3000 nM calcium.

Figure 4:
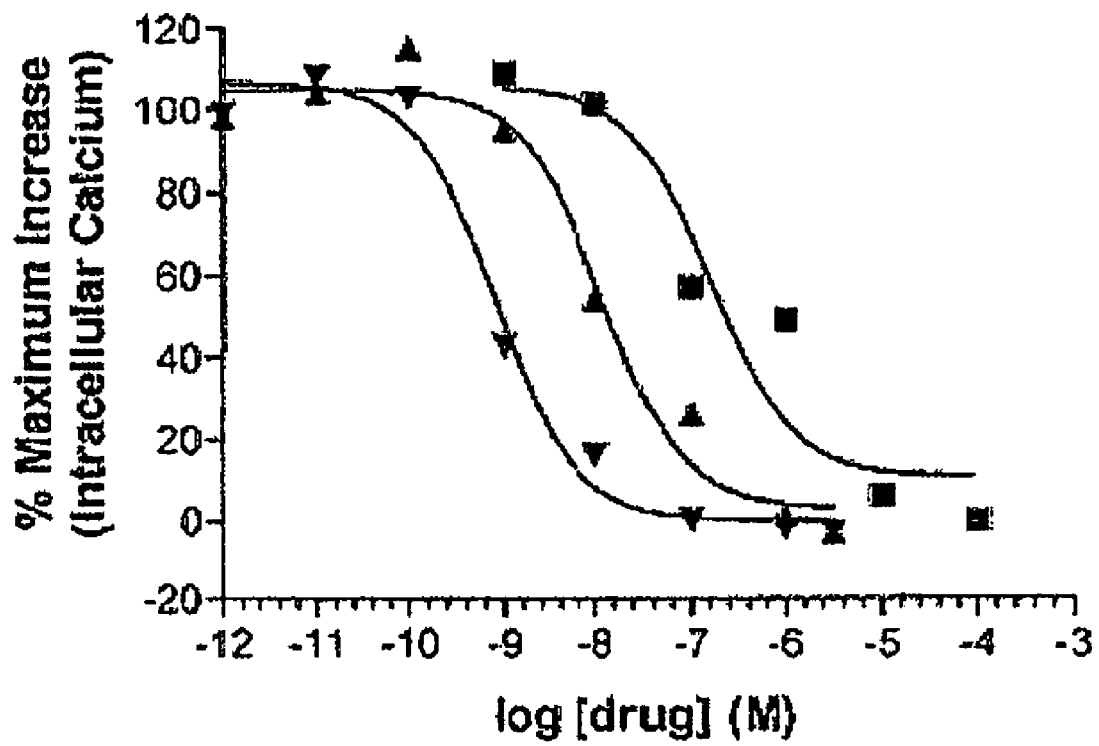
FIG. 4 depicts dose response curves for Compound Ia compared with naloxone and CTOP obtained from the opioid functional antagonist assay described in Example 5 part F.

Results of the opioid functional (calcium) antagonist assay for Compound Ia are set forth in Table 4-1 and Table 4-2. Dose response curves for Compound Ia compared with naloxone and CTOP are depicted in FIG. 4.

TABLE 4-1

$IC_{50}$ from Opioid, Mu (Human Recombinant), Functional (calcium) Antagonist Assay.

| Agent | $IC_{50}$ |
|---|---|
| Compound Ia | 170 nM |

TABLE 4-2

Dose Response Results

| Log (Agent Molarity) | Agent | | |
|---|---|---|---|
| | CTOP (Control) | Naloxone (Control) | Compound Ia |
| −4 | — | — | 0 |
| −5 | — | — | 6 |
| −5.5 | −3 | −3 | — |
| −6.0 | 1 | −2 | 49 |
| −7.0 | 26 | 0 | 57 |
| −8.0 | 54 | 16 | 101 |
| −9.0 | 95 | 43 | 109 |
| −10.0 | 115 | 103 | — |
| −11.0 | 104 | 108 | — |
| Blank | 98 | 99 | — |

G. Administration in GI-Physiology Altered Dogs.

A 50 mg capsule formulation of Compound Ia was screened in gastrointestinal (GI) physiology regulated male beagle dogs. Atropine (~20 μg/kg; IV) and pentagastrin (~10 μg/kg; IM) were administered 15 minutes prior to formulation administration and another dose of pentagastrin (10 μg/kg; IM) was administered 30 minutes post dose. Atropine slows down canine GI motility and pentagastrin decreases pH resulting in GI conditions almost similar to that of humans. The capsules (50 mg Compound Ia) were dosed to six dogs (9.4-13.7 kg) via oral administration following an overnight fast and blood samples were drawn at 0 (predose), 0.5, 1, 2, 3, 4, 6, 8, 12, 24 and 48 hours after dosing; plasma was separated and assayed for Compound Ia content. All dogs were fed 4 hours post dose.

50 mg Compound Ia capsule contained neat 51.5 mg of Compound Ia 97% purity (50 mg of Compound Ia), filled in #AA-DB HGC Swedish orange capsule.

Bioanalytical results were received and a preliminary PK assessment was performed. Individual dog plasma Compound Ia concentration-time profiles were subjected to non-compartmental pharmacokinetic analyses (WinNonlin, Model 200). The following pharmacokinetic parameters were determined for each dog, and descriptive statistics were calculated: AUC, $C_{max}$, and $t_{max}$. The results are summarized in Table 5 below.

TABLE 5

| Compound Ia Pharmacokinetic Parameters Following a Single 50 mg Capsule. | | | | | | | |
|---|---|---|---|---|---|---|---|
| Compound | Treatment | Animal | Dose (50 mg capsule) | Cmax (ng/mL) | Tmax (Hr) | Half-Life (hrs) | AUC last (Hr * ng/mL) | AUC 0-inf (Hr * ng/mL) |
| Ia | PO | Dog 1 | 50 | 825 | 2 | 3.9 | 4631 | 4690 |
| Ia | PO | Dog 2 | 50 | 1673 | 3 | 2.8 | 7719 | 7736 |
| Ia | PO | Dog 3 | 50 | 1576 | 1 | 1.1 | 6210 | 6220 |
| | | N | | 3 | 3 | 3 | 3 | 3 |
| | | Mean | | 1358 | 2 | 2.6 | 6187 | 6215 |
| | | SD | | 464.1 | 1.0 | 1.4 | 1544.3 | 1522.7 |
| | | Median | | 1576 | 2.0 | 2.8 | 6210 | 6220 |
| | | CV % | | 34 | 50 | 55 | 25 | 24 |

One skilled in the art will readily ascertain the essential characteristics of the invention, and understand that the foregoing description and examples are illustrative of practicing the provided invention. Those skilled in the art will be able to ascertain using no more than routine experimentation, many variations of the detail presented herein may be made to the specific embodiments of the invention described herein without departing from the spirit and scope of the present invention.

Patents, patent applications, publications, and the like are cited throughout the application. The disclosures of each of these documents are incorporated herein by reference in their entirety.

What is claimed is:

1. A compound of formula I:

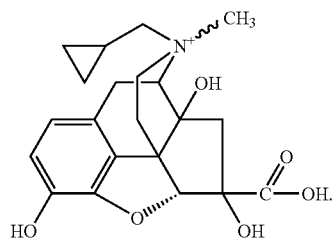

I

2. The compound according to claim 1, wherein said compound is:

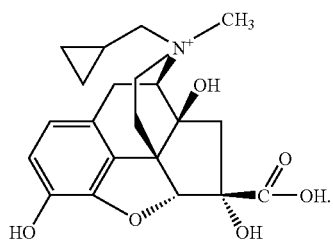

Compound I-1

3. A compound of formula I:

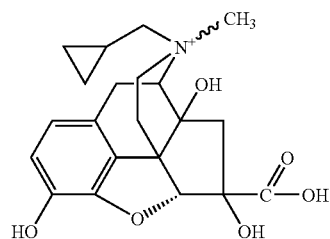

I or a pharmaceutically acceptable salt thereof.

4. The compound according to claim 3, wherein said compound is a pharmaceutically acceptable salt selected from the group consisting of a chloride, sulfate, bisulfate, hydroxyl, tartrate, nitrate, citrate, bitartrate, carbonate, phosphate, malate, maleate, bromide, iodide, fluoride, fumarate sulfonate, methylsulfonate, formate, carboxylate, sulfate, methylsulfate and succinate.

5. A compound of formula Ia:

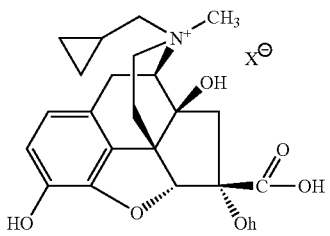

Ia wherein $X^-$ is a suitable anion other than trifluoroacetate.

6. The compound according to claim 5, wherein $X^-$ is selected from the group consisting of a chloride, sulfate, bisulfate, hydroxyl, tartrate, nitrate, citrate, bitartrate, carbonate, phosphate, malate, maleate, bromide, iodide, fluoride, fumarate sulfonate, methylsulfonate, formate, carboxylate, sulfate, methylsulfate and succinate.

7. The compound of claim 6, wherein the compound is in a solid form.

8. The compound of claim 6, wherein the compound is in solution.

9. A pharmaceutically acceptable composition comprising a therapeutically effective amount of a compound of formula I:

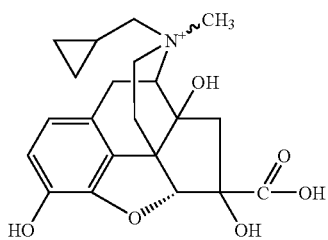

or a pharmaceutically acceptable salt thereof, and a pharmaceutically acceptable carrier.

10. The composition according to claim 9, formulated for administration to a human subject.

11. The composition according to claim 9, further comprising methylnaltrexone.

12. A method of reducing one or more side effects of opioid therapy in a subject receiving opioid treatment comprising administering to the subject a composition according to claim 9, wherein the side effect is inhibition of intestinal motility, constipation, inhibition of gastrointestinal motility, inhibition of gastric emptying, nausea, emesis, dysphoria, urinary retention, or pruritis.

13. The method according to claim 12, wherein the side effect is caused, mediated, or exacerbated by opioid receptor activity.

14. The method of claim 12, wherein the subject is a patient receiving short term opioid administration or a patient receiving chronic opioid administration.

* * * * *